United States Patent
Wang et al.

(10) Patent No.: US 12,306,178 B2
(45) Date of Patent: May 20, 2025

(54) MAGNETIC CHEMILUMINESCENCE IMMUNOASSAY KIT BASED ON BIFUNCTIONAL FUSION PROTEIN FOR MYCOTOXINS, AND USE THEREOF

(71) Applicant: ACADEMY OF NATIONAL FOOD AND STRATEGIC RESERVES ADMINISTRATION, Beijing (CN)

(72) Inventors: Songxue Wang, Beijing (CN); Hongmei Liu, Beijing (CN); Jin Ye, Beijing (CN); Baoxia Ni, Beijing (CN); Jinnan Chen, Beijing (CN)

(73) Assignee: ACADEMY OF NATIONAL FOOD AND STRATEGIC RESERVES ADMINISTRATION, Beijing (CN)

( * ) Notice: Subject to any disclaimer, the term of this patent is extended or adjusted under 35 U.S.C. 154(b) by 0 days.

(21) Appl. No.: 18/722,997

(22) PCT Filed: Feb. 17, 2023

(86) PCT No.: PCT/CN2023/076761
§ 371 (c)(1),
(2) Date: Jun. 21, 2024

(87) PCT Pub. No.: WO2023/155876
PCT Pub. Date: Aug. 24, 2023

(65) Prior Publication Data
US 2025/0012789 A1    Jan. 9, 2025

(30) Foreign Application Priority Data
Feb. 21, 2022   (CN) .......................... 202210155141.5

(51) Int. Cl.
| | |
|---|---|
| *G01N 33/543* | (2006.01) |
| *C07K 16/14* | (2006.01) |
| *C07K 19/00* | (2006.01) |
| *C12N 15/62* | (2006.01) |
| *G01N 33/53* | (2006.01) |
| *G01N 33/58* | (2006.01) |

(52) U.S. Cl.
CPC ....... *G01N 33/54326* (2013.01); *C07K 16/14* (2013.01); *C07K 19/00* (2013.01); *C12N 15/62* (2013.01); *G01N 33/5308* (2013.01); *G01N 33/581* (2013.01); *C07K 2319/55* (2013.01)

(58) Field of Classification Search
CPC .... C07K 16/14; C07K 19/00; C07K 2319/55; C12N 15/62; G01N 33/5308; G01N 33/54326; G01N 33/581
See application file for complete search history.

(56) References Cited

FOREIGN PATENT DOCUMENTS

| | | | |
|---|---|---|---|
| CN | 102608324 | A | 7/2012 |
| CN | 103014012 | A | 4/2013 |
| CN | 107543918 | A * | 1/2015 |
| CN | 105929156 | A | 9/2016 |
| CN | 108088992 | A | 5/2018 |
| CN | 113621079 | A | 11/2021 |
| CN | 114594262 | A | 6/2022 |
| JP | 07289264 | A | 11/1995 |

OTHER PUBLICATIONS

Liu et al., "Development of a Nanobody-Alkaline Phosphatase Fusion Protein and Its Application in a Highly Sensitive Direct Competitive Fluorescence Enzyme Immunoassay for Detection of Ochratoxin A in Cereal," Anal. Chem., 2015, vol. 87, pp. 1387-1394.*
CN107543918 A, published Jan. 5, 2018, Machine translation.*
Zhao et al., "A novel nanobody and mimotope based immunoassay for rapid analysis of aflatoxin B1," Talanta, Apr. 1, 2019, vol. 195, pp. 55-61.*
He et al., "Nanobody-Based Enzyme Immunoassay for Aflatoxin in Agro-Products with High Tolerance to Cosolvent Methanol," Anal. Chem., 2014, vol. 86, pp. 8873-8880.*
International Search Report of PCT/CN2023/076761 dated Apr. 11, 2023, 10 pages.
Chinese First Office Action (Chinese and English) CN202210155141.5 dated Aug. 5, 2022.

* cited by examiner

*Primary Examiner* — Galina M. Yakovleva
(74) *Attorney, Agent, or Firm* — Rankin, Hill & Clark LLP

(57) ABSTRACT

Disclosed is a magnetic chemiluminescence immunoassay kit based on a bifunctional fusion protein for mycotoxins, and a use thereof. The kit includes streptavidin magnetic particles, a biotin-labeled mycotoxin antigen, a mycotoxin standard solution, a mycotoxin single-chain variable fragment (ScFV)-alkaline phosphatase bifunctional fusion protein, a sample diluent, a washing solution and a substrate solution. The kit of the disclosure integrates chemiluminescence, magnetic particle separation and gene engineering technologies, thereby quickly, accurately and automatically testing the mycotoxins; and edible oil can be directly added for test without operations of extraction, centrifugation, etc., thereby reducing operation errors of testing personnel, reducing capability requirements on the testing personnel, significantly improving testing efficiency of large quantities of samples at a grassroots level, and providing a powerful means for mycotoxin testing and monitoring.

17 Claims, 1 Drawing Sheet
Specification includes a Sequence Listing.

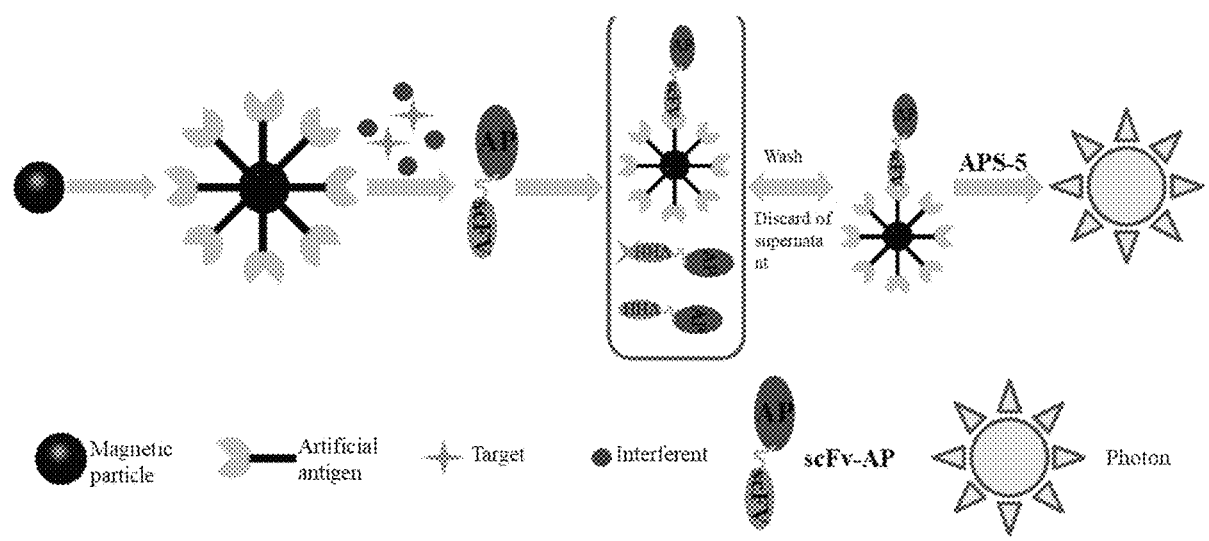

SEQUENCE LISTING

```
Sequence total quantity: 8
SEQ ID NO: 1              moltype = AA  length = 581
FEATURE                   Location/Qualifiers
source                    1..581
                          mol_type = protein
                          organism = synthetic construct
SEQUENCE: 1
MQLQLVESGG GLVQAGGSLR LSCAASGRTF SSYAMGWFRQ APGKEREFVA VVNWSGRRTY    60
YADSVKGRFT ISRDNAKNTV YLQMNSLKPE DTAVYNCAAG KWDGSYYGAP DYWGQGTQVT   120
VSSLEHHHHH HNTPEMPVLE NRAAQGNITA PGGARRLTGD QTAALRNSLS DKPAKNIILL   180
IGDGMGDSEI TAARNYAEGA GGFFKGIDAL PLTGQYTHYA LNKKTGKPDY VTDSAASATA   240
WSTGVKTYNG ALGVDIHEKD HPTILEMAKA AGLATGNVST AELQDATPAA LVAHVTSRKC   300
YGPSATSQKC PGNALEKGGK GSITEQLLNA RADVTLGGGA KTFAETATAG EWQGKTLREE   360
AEARGYQLVS DAASLNSVTE ANQQKPLLGL FADGNMPVRW LGPKATYHGN IDKPAVTCTP   420
NPQRNDSVPT LAQMTDKAIE LLSKNEKGFF LQVEGASIDK QNHAANPCGQ IGETVDLDEA   480
```

```
VQRALEFAKK EGNTLVIVTA DHAHASQIVA PDTKAPGLTQ ALNTKDGAVM VMSYGNSEED    540
SQEHTGSQLR IAAYGPHAAN VVGLTDQTDL FYTMKAALGL K                       581

SEQ ID NO: 2            moltype = AA  length = 570
FEATURE                 Location/Qualifiers
source                  1..570
                        mol_type = protein
                        organism = synthetic construct
SEQUENCE: 2
MEVSSLTNED SAVYYCRPGQ GLEWIGAISL GNSGAWYNQK FKDKAKLTAV TSTNTAYTRE    60
DYYGQGFPYW GQGTTVTVSS MAQVQLQQSG TVLARPGTSV KMSCKTSDYT FTNCWIHWIK    120
QTPEMPVLEN RAAQGNITAP GGARRLTGDQ TAALRNSLSD KPAKNIILLI GDGMGDSEIT    180
AARNYAEGAG GFFKGIDALP LTGQYTHYAL NKKTGKPDYV TDSAASATAW STGVKTYNGA    240
LGVDIHEKDH PTILEMAKAA GLATGNVSTA ELQDATPAAL VAHVTSRKCY GPSATSQKCP    300
GNALEKGGKG SITEQLLNAR ADVTLGGGAK TFAETATAGE WQGKTLREEA EARGYQLVSD    360
AASLNSVTEA NQQKPLLGLF ADGNMPVRWL GPKATYHGNI DKPAVTCTPN PQRNDSVPTL    420
AQMTDKAIEL LSKNEKGFFL QVEGASIDKQ NHAANPCGQI GETVDLDEAV QRALEFAKKE    480
GNTLVIVTAD HAHASQIVAP DTKAPGLTQA LNTKDGAVMV MSYGNSEEDS QEHTGSQLRI    540
AAYGPHAANV VGLTDQTDLF YTMKAALGLK                                    570

SEQ ID NO: 3            moltype = AA  length = 566
FEATURE                 Location/Qualifiers
source                  1..566
                        mol_type = protein
                        organism = synthetic construct
SEQUENCE: 3
GTEVVKPGSV KLSCKQVKLQ QSASGYIWIG WIFPGEGSTE YNEKFKGRAT LSVDKSSSTF    60
TSYDIDWVRQ TPEQGLEAYM ELRYFDLWGQ GTTVTVSSTR LTSEDSAVYF CARGDYYTPE    120
MPVLENRAAQ GNITAPGGAR RLTGDQTAAL RNSLSDKPAK NIILLIGDGM GDSEITAARN    180
YAEGAGGFFK GIDALPLTGQ YTHYALNKKT GKPDYVTDSA ASATAWSTGV KTYNGALGVD    240
IHEKDHPTIL EMAKAAGLAT GNVSTAELQD ATPAALVAHV TSRKCYGPSA TSQKCPGNAL    300
EKGGKGSITE QLLNARADVT LGGGAKTFAE TATAGEWQGK TLREEAEARG YQLVSDAASL    360
NSVTEANQQK PLLGLFADGN MPVRWLGPKA TYHGNIDKPA VTCTPNPQRN DSVPTLAQMT    420
DKAIELLSKN EKGFFLQVEG ASIDKQNHAA NPCGQIGETV DLDEAVQRAL EFAKKEGNTL    480
VIVTADHAHA SQIVAPDTKA PGLTQALNTK DGAVMVMSYG NSEEDSQEHT GSQLRIAAYG    540
PHAANVVGLT DQTDLFYTMK AALGLK                                        566

SEQ ID NO: 4            moltype = AA  length = 602
FEATURE                 Location/Qualifiers
source                  1..602
                        mol_type = protein
                        organism = synthetic construct
SEQUENCE: 4
MAQVQLQQSG TVLVQAGGSL RLSCALQMNS LKPEDREFVA VVNWSGRRTY YADSVKGRFT    60
ISRDNAKNTV YNCAAGKQVK LQQSASGYIW IGWKWDGSYY GAPDYWGQGT QVTSVTAVYA    120
SGRAPGKEKL SCKSVKLSCQ VKLQQSASGY IWITPEMPVL ENRAAQGNIT APGGARRLTG    180
DQTAALRNSL SDKPAKNIIL LIGDGMGDSE ITAARNYAEG AGGFFKGIDA LPLTGQYTHY    240
ALNKKTGKPD YVTDSAASAT AWSTGVKTYN GALGVDIHEK DHPTILEMAK AAGLATGNVS    300
TAELQDATPA ALVAHVTSRK CYGPSATSQK CPGNALEKGG KGSITEQLLN ARADVTLGGG    360
AKTFAETATA GEWQGKTLRE EAEARGYQLV SDAASLNSVT EANQQKPLLG LFADGNMPVR    420
WLGPKATYHG NIDKPAVTCT PNPQRNDSVP TLAQMTDKAI ELLSKNEKGF FLQVEGASID    480
KQNHAANPCG QIGETVDLDE AVQRALEFAK KEGNTLVIVT ADHAHASQIV APDTKAPGLT    540
QALNTKDGAV MVMSYGNSEE DSQEHTGSQL RIAAYGPHAA NVVGLTDQTD LFYTMKAALG    600
LK                                                                  602

SEQ ID NO: 5            moltype = AA  length = 581
FEATURE                 Location/Qualifiers
source                  1..581
                        mol_type = protein
                        organism = synthetic construct
SEQUENCE: 5
TSYDIDWVRQ LKGKWDGTPE QGLTNEDSPE DTAAQQSGTV LRLSCAASGR TFSSYAMGGA    60
KNTVYLQMNS SYYGAWFRQA PGKEAVYYCR PGQGLEWIQL RERTYYADSV KPDYWGQGTQ    120
VFVAVVNWSG RTTPEMPVLE NRAAQGNITA PGGARRLTGD QTAALRNSLS DKPAKNIILL    180
IGDGMGDSEI TAARNYAEGA GGFFKGIDAL PLTGQYTHYA LNKKTGKPDY VTDSAASATA    240
WSTGVKTYNG ALGVDIHEKD HPTILEMAKA AGLATGNVST AELQDATPAA LVAHVTSRKC    300
YGPSATSQKC PGNALEKGGK GSITEQLLNA RADVTLGGGA KTFAETATAG EWQGKTLREE    360
AEARGYQLVS DAASLNSVTE ANQQKPLLGL FADGNMPVRW LGPKATYHGN IDKPAVTCTP    420
NPQRNDSVPT LAQMTDKAIE LLSKNEKGFF LQVEGASIDK QNHAANPCGQ IGETVDLDEA    480
VQRALEFAKK EGNTLVIVTA DHAHASQIVA PDTKAPGLTQ ALNTKDGAVM VMSYGNSEED    540
SQEHTGSQLR IAAYGPHAAN VVGLTDQTDL FYTMKAALGL K                       581

SEQ ID NO: 6            moltype = AA  length = 589
FEATURE                 Location/Qualifiers
source                  1..589
                        mol_type = protein
                        organism = synthetic construct
SEQUENCE: 6
QVQLVESGGL GLVQAGGSLR LSCANSSTVS IARIGWYRQA PRELVAAINI YNSRDSVQGR    60
```

```
FTSRDNAKRT VYLQMNNLKP EDTAVYYCMQ LQLVESGGGL VQAGGSLRLS CAASLVQAGG    120
SLRLSCAASA GGSLRLRLSC TPEMPVLENR AAQGNITAPG GARRLTGDQT AALRNSLSDK    180
PAKNIILLIG DGMGDSEITA ARNYAEGAGG FFKGIDALPL TGQYTHYALN KKTGKPDYVT    240
DSAASATAWS TGVKTYNGAL GVDIHEKDHP TILEMAKAAG LATGNVSTAE LQDATPAALV    300
AHVTSRKCYG PSATSQKCPG NALEKGGKGS ITEQLLNARA DVTLGGGAKT FAETATAGEW    360
QGKTLREEAE ARGYQLVSDA ASLNSVTEAN QQKPLLGLFA DGNMPVRWLG PKATYHGNID    420
KPAVTCTPNP QRNDSVPTLA QMTDKAIELL SKNEKGFFLQ VEGASIDKQN HAANPCGQIG    480
ETVDLDEAVQ RALEFAKKEG NTLVIVTADH AHASQIVAPD TKAPGLTQAL NTKDGAVMVM    540
SYGNSEEDSQ EHTGSQLRIA AYGPHAANVV GLTDQTDLFY TMKAALGLK               589

SEQ ID NO: 7            moltype = AA  length = 131
FEATURE                 Location/Qualifiers
source                  1..131
                        mol_type = protein
                        organism = synthetic construct
SEQUENCE: 7
MQLQLVESGG GLVQAGGSLR LSCAASGRTF SSYAMGWFRQ APGKEREFVA VVNWSGRRTY     60
YADSVKGRFT ISRDNAKNTV YLQMNSLKPE DTAVYNCAAG KWDGSYYGAP DYWGQGTQVT    120
VSSLEHHHHH H                                                        131

SEQ ID NO: 8            moltype = DNA  length = 392
FEATURE                 Location/Qualifiers
source                  1..392
                        mol_type = other DNA
                        organism = synthetic construct
SEQUENCE: 8
atgcagctgc aactggttga atctggtggt ggtctggttc aagcaggtgg ttccctgcgt     60
ctgtcttgcg ctgcgagcgg tcgtaccttc tctagctacg gatgggttgg ttccgtcagg    120
ctccgggtaa agaacgcgag ttcgttgcgg tagttaactg gtctggtcgt cgcacttact    180
acgctgactc cgtaaaaggt cgttttacca tttctcgtga caatgcaaaa aacaccgtct    240
acctgcagat gaattccctg aaaccggaag ataccgccgt ctacaactgc gccgcgggta    300
aatgggatgg ttcttactac ggcgcaccag attactgggg tcagggcacc caggttactg    360
ttagctctct ggagcaccac catcaccacc ac                                 392
```

MAGNETIC CHEMILUMINESCENCE IMMUNOASSAY KIT BASED ON BIFUNCTIONAL FUSION PROTEIN FOR MYCOTOXINS, AND USE THEREOF

TECHNICAL FIELD

The disclosure belongs to the technical field of food safety testing, and relates to a magnetic chemiluminescence immunoassay kit based on a bifunctional fusion protein for mycotoxins, and a use thereof.

BACKGROUND

Mycotoxins, secondary metabolites produced by toxigenic fungi under certain environmental conditions, have widely polluted plant-based products such as agricultural products, food, traditional Chinese medicine material and feed. Deoxynivalenol (DON) (which is also known as vomitoxin), aflatoxin B1 (AFB1), aflatoxin B2 (AFB2), aflatoxin G1 (AFG1), aflatoxin G2 (AFG2), ochratoxin A (OTA), fumonisin B1 (FB1), fumonisin B2 (FB2), zearalenone (ZEN), T-2 toxin, HT-2 toxin or aflatoxin M1 (AFM1), patulin, etc. are common mycotoxins in the agricultural products, the food and the feed. The mycotoxins can cause acute or chronic intoxication in humans and animals, which can damage livers, kidneys, nerve tissues, hematopoietic tissues and skin tissues of bodies, thereby producing serious effects on human and animal health. Owning to the harm of the mycotoxins, countries around the world have imposed strict limits on their content. It is of great significance to conduct research on mycotoxin residue pollution and develop highly-sensitive, low-cost and reliable automatic test technologies in ensuring the quality and safety of the agricultural products, the food, the traditional Chinese medicine and the feed, breaking down foreign technological barriers, protecting China's economic interests in international trade, and increasing export earnings.

At present, thin-layer chromatography, high-performance liquid chromatography, enzyme-linked immunosorbent assay, capillary electrophoresis, and liquid chromatography mass spectrometry serve to test the mycotoxins. The thin-layer chromatography serves to test the mycotoxins at the earliest, and has the advantages of suitability for operation of personnel without being specially trained, low cost and no need for expensive instruments. However, the thin-layer chromatography has tedious sample treatment, a complex experimental process, a long required test cycle, and easy interference from impurities. The use of visual semi-quantitative measurement in the test process has the disadvantages of significant subjective influence and low sensitivity, which can no longer satisfy modern test requirements. The enzyme-linked immunosorbent assay has the advantages of excellent specificity test, high sensitivity and low test cost, and is suitable for screening and surveying a large number of samples in a grassroots institution, which can greatly save time and cost. However, the enzyme-linked immunosorbent assay mainly causes false positives easily. Consequently, it mainly serves to screen and test the samples at a grassroots level. Instrument analysis methods such as the high-performance liquid chromatography, the capillary electrophoresis and the liquid chromatography mass spectrometry have the advantages of high accuracy, high sensitivity and micro determination, making them common in test of toxins in the food. However, with their high requirements for sample purity and the need for some pretreatment processes, the instrument analysis methods have high test cost and a long cycle, resulting in an incapability of satisfying the requirements of quickly screening a large quantities of samples. Magnetic particles have superparamagnetic microparticle properties and magnetic particle field responsiveness in a magnetic particle field. The magnetic particles are used as a solid-phase carrier for immune detection, which will greatly increase a surface area of reaction, and make it easier to separate a solid phase from a liquid phase, thereby improving sensitivity of test. Small magnetic particles are used as the solid phase, which can increase a surface area of a coating, thereby increasing adsorption capacity of antigens or antibodies, which not only increases a reaction speed, but also makes cleaning and separation easier. At present, a method for preparation an immune enzyme-labeled reagent couples antibodies with enzymes according to a chemical labeling method, such as use of a bifunctional reagent, such as glutaraldehyde, periodate, {N-Succinimidyl 4-(N-maleimidomethyl)cyclohexane-1-carboxylate}(SMCC) reagent and a 2-iminothiolane (2-IT) reagent (iminothiophene hydrochloride). However, a chemical coupling method has complex operation and low coupling efficiency. With an unfixed coupling site and a harsh condition, it is easy to reduce activity of the antibodies or the enzymes, and conjugates of the antibodies and the enzymes are uneven. Consequently, it is necessary to separate and remove unbound enzymes and antibodies. Moreover, free antibodies will compete with enzyme-labeled antibodies for corresponding antigens, which reduces an amount of the enzyme-labeled antibodies bound to the solid phase, thereby reducing sensitivity of test. As a result, it is crucial to remove the unbound antibodies.

With the significant harm of the mycotoxins, it is of great significance to find a simple, quick, accurate and automatic test method in study of mycotoxin test and pollution control.

SUMMARY

A first objective of the disclosure is to provide a magnetic chemiluminescence immunoassay kit for mycotoxins, which integrates chemiluminescence, magnetic particle separation and gene engineering technologies, and has excellent accuracy, sensitivity and repeatability.

A second objective of the disclosure is to provide a use of the kit in test of mycotoxins.

In order to achieve the above objectives, the disclosure uses the following technical solutions:

In a first aspect, the disclosure provides a magnetic chemiluminescence immunoassay kit for mycotoxins. The kit includes streptavidin magnetic particles, a biotin-labeled mycotoxin antigen, a mycotoxin standard solution, a mycotoxin single-chain variable fragment (ScFV)-alkaline phosphatase (ScFV-AP) bifunctional fusion protein, a sample diluent, a washing solution and a substrate solution.

The disclosure covalently binds —COOH active groups provided by surface organic matters with streptavidin —NH2 by taking micron-sized magnetic particles as a carrier, and carries out "bridging" through biotin-streptavidin to form a magnetic particle-streptavidin-biotin-mycotoxin-ScFV-AP bifunctional fusion protein complex. The technology has the novelty: (1) A contact area between an antigen and an antibody and a light-emitting area of a substrate are increased by using the magnetic particles as the solid-phase carrier, thereby improving sensitivity of reaction; and the magnetic particles have an effect of stirring and separating the magnetic particle-streptavidin-biotin-mycotoxin-ScFV-AP bifunctional fusion protein complex from a mycotoxin-ScFV-AP bifunctional fusion protein complex through a rotating magnetic particle field. (2) The ScFV-AP bifunctional fusion protein improves specificity and stability of reaction. (3) Edible oil can be directly added for test without operations of extraction, centrifugation, etc., thereby greatly improving testing efficiency.

Further, the ScFV-AP bifunctional fusion protein is obtained by fusion expression of a mycotoxin single-chain variable fragment (ScFV) and an alkaline phosphatase (AP) by using the AP as a catalyst for bioluminescence.

Preferably, the mycotoxin single-chain variable fragment (ScFV) is selected from heavy chain antibodies of camelids or sharks.

Further, the mycotoxin single-chain variable fragment (ScFV)-alkaline phosphatase bifunctional fusion protein of the disclosure may have any one or more of the following amino acid sequences:
- an amino acid sequence of an aflatoxin B1 single-chain variable fragment (ScFV)-alkaline phosphatase bifunctional fusion protein shown as SEQ ID NO:1;
- an amino acid sequence of a deoxynivalenol single-chain variable fragment (ScFV)-alkaline phosphatase bifunctional fusion protein shown as SEQ ID NO:2;
- an amino acid sequence of a zearalenone single-chain variable fragment (ScFV)-alkaline phosphatase bifunctional fusion protein shown as SEQ ID NO:3;
- an amino acid sequence of a T-2 single-chain variable fragment (ScFV)-alkaline phosphatase bifunctional fusion protein shown as SEQ ID NO:4;
- an amino acid sequence of a fumonisin B1 single-chain variable fragment (ScFV)-alkaline phosphatase bifunctional fusion protein shown as SEQ ID NO:5; and
- an amino acid sequence of an ochratoxin A single-chain variable fragment (ScFV)-alkaline phosphatase bifunctional fusion protein shown as SEQ ID NO:6.

According to a particular embodiment of the disclosure, corresponding biotin-labeled mycotoxin antigens, mycotoxin standard solutions, and mycotoxin single-chain variable fragment (ScFV)-alkaline phosphatase bifunctional fusion proteins are selected according to types of toxins to be tested. For example, when deoxynivalenol is tested, the kit of the present application should include a biotin-labeled deoxynivalenol antigen, a deoxynivalenol standard solution, and a deoxynivalenol single-chain variable fragment (ScFV)-alkaline phosphatase bifunctional fusion protein.

Further, the ScFV-AP bifunctional fusion protein may be synthesized according to the amino acid sequence provided above, or may be prepared through the following method:
(1) designing and synthesizing a mycotoxin single-chain variable fragment (ScFV) gene: optimizing, according to an amino acid sequence of the mycotoxin single-chain variable fragment, a structure of a gene to efficiently express the gene in *Escherichia coli* (*E. coli*) as follows: using a preferred codon of the *E. coli*, eliminating a possible secondary structure, achieving GC/AT balance, and designing and synthesizing a nucleotide fragment of the mycotoxin single-chain variable fragment (ScFV) gene;
(2) constructing a mycotoxin single-chain variable fragment (ScFV)-alkaline phosphatase bifunctional fusion expression vector: cloning the mycotoxin single-chain variable fragment (ScFV) gene synthesized in step (1) and an alkaline phosphatase gene into a prokaryotic expression vector to construct the mycotoxin single-chain variable fragment (ScFV)-alkaline phosphatase bifunctional fusion expression vector;
(3) expressing the mycotoxin single-chain variable fragment (ScFV)-alkaline phosphatase bifunctional fusion protein: transforming the bifunctional fusion expression vector into competent cells of an expression strain *E. coli* BL21 or Rosetta™ DE3, inducing expression, collecting bacterial cells, adding a bacterial protein extraction reagent, and centrifugally collecting supernatant containing a soluble protein; and
(4) purifying the bifunctional fusion protein: purifying the fusion protein using a $Ni^{2+}$-NTA affinity column.

The disclosure can overcome various defects of a chemical labeling method and obtain an enzyme-labeled antibody having high specific activity by means of fusion expression of the mycotoxin single-chain variable fragment (ScFV) and the alkaline phosphatase. The fusion protein prepared can be applied to the field of immunodiagnosis, such as chemiluminescence immunoassay, enzyme linked immunosorbent assay or enzyme fluorescence immunoassay, as a test reagent. Compared with a traditional chemical coupling method of an alkaline phosphatase, the ScFV-AP bifunctional fusion protein has the following advantages: (1) The traditional chemical coupling method has a long process flow, a complex coupling process and a severe condition, resulting in an unstable process, low yield of a coupling product and poor stability between batches. The fusion expression of the mycotoxin single-chain variable fragment (ScFV) and the alkaline phosphatase is simple and has a stable process, thereby avoiding tedious and inefficient chemical crosslinking of the enzyme and the protein. (2) In order to obtain the excellent coupling product, the traditional chemical coupling method usually needs to purify a target coupling product to remove unlinked enzyme and antibody molecules, has incomplete purification, and thus may produce a false positive result during test. The fusion expression of the mycotoxin single-chain variable fragment (ScFV) and the alkaline phosphatase overcomes the disadvantage. (3) An enzyme and antibody complex after coupling is heterogeneous in the traditional chemical coupling method. A ratio of the mycotoxin single-chain variable fragment (ScFV) to a monomer alkaline phosphatase molecule in a fusion expression product of the mycotoxin single-chain variable fragment (ScFV) and the alkaline phosphatase is 1:1 or 1:2, and the mycotoxin single-chain variable fragment (ScFV) can be separated from the monomer alkaline phosphatase molecule during nickel column purification, thereby ensuring a homogeneous enzyme and antibody complex. (4) In the traditional chemical coupling method, a binding position of a coupling chemical active reagent is unfixed, and may be bound to an antibody variable region, thereby affecting binding of the antibody to the target antigen; alternatively, a coupling chemical active reagent is bound to a vicinity of an alkaline phosphatase active site, thereby affecting bonding of the alkaline phosphatase to a substrate; and both the cases can cause reduction in the activity of a coupling complex, and thus a false negative result is easily obtained during test. The fusion expression mode of the mycotoxin single-chain variable fragment (ScFV) and the alkaline phosphatase does not affect activity of the mycotoxin single-chain variable fragment (ScFV) and the alkaline phosphatase. (5) The ScFV-AP fusion protein according to the disclosure has excellent specificity and signal amplification, and a hypersensitive bioluminescence immunoassay kit is established through the ScFV-AP fusion protein, is configured to test contents of mycotoxins in substrates such as grain and oil, food, feed and Chinese herbal medicine, and has excellent application value and prospect. (6) Compared with a single-chain variable fragment, the single-chain variable fragment (ScFV) has great advantages in aspects of antibody stability, batch-to-batch repeatability, titer, etc., and all other antibody molecules apart from those indicated in the disclosure can produce an alkaline phosphatase coupled molecule in this way.

Further, peripheries of magnetic particles are coated with polystyrene or dextran by taking a ferroferric oxide or ferric oxide superparamagnetic material as a core, the magnetic particles are activated according to a physical or chemical method to generate —NH2, tosyl, —COOH or —CH(O) groups on surfaces of the magnetic particles, and the magnetic particles have a particle size ranging from 1 μm to 2 μm.

Further, the streptavidin magnetic particles are obtained by coupling streptavidin with magnetic particles.

Further, the biotin-labeled mycotoxin antigen is obtained by coupling mycotoxins with bovine serum albumin, and then coupling an obtained bovine serum albumin-mycotoxin complex with biotin.

Further, the mycotoxin standard solution is prepared by dissolving a mycotoxin standard into a methanol-water mixed solution. According to a particular embodiment of the disclosure, the mycotoxin standard solution in the kit can be a mother solution having a certain concentration, is diluted into standard working solutions having different concentrations according to requirements during use, and is configured to draw a standard curve; or a series of concentrations of mycotoxin standard solutions may be directly subpackaged and placed in the kit, and are configured to draw standard curves.

Preferably, a volume ratio of methanol to water in the methanol-water mixed solution is 50:50.

Further, the substrate solution is (4-chlorophenylmercapto)(10-methyl-9,10-dihydroacridine methylene) disodium phosphate salt solution having a concentration ranging from 0.5 mmol/L to 2 mmol/L.

Preferably, the sample diluent consists of 0.01 M phosphate buffer, 0.1% Tween®-20 and 0.5% bovine serum albumin.

Preferably, the washing solution consists of 0.01 M tris-HCl buffer and 0.1% Tween®-20.

Further, the kit further includes a reaction tube; and preferably, the reaction tube is made of transparent polystyrene, polyethylene, polypropylene or glass.

In a second aspect, the disclosure further sets forth a use of the kit in test of mycotoxins, particularly, a use of the kit in test of mycotoxins in edible oil, food, grain, feed or Chinese herbal medicine.

Further, the edible oil includes one of peanut oil, corn oil, soybean oil, rapeseed oil, sunflower oil, rapeseed oil, sesame oil and olive oil.

Further, the mycotoxins include one or more of aflatoxin, zearalenone, deoxynivalenol, fumonisin, ochratoxin A and T-2 toxin.

According to the disclosure, the mycotoxins in the food, the agricultural products and the feed are determined according to an indirect competition principle, and a biotin-labeled mycotoxin antigen working solution, the ScFV-AP bifunctional fusion protein and a sample to be tested are added into a streptavidin magnetic particle suspension. Mycotoxin in the sample and the biotin-labeled mycotoxin antigen compete for a limited number of ScFV-AP bifunctional fusion proteins, and forms a magnetic particle-streptavidin-biotin-mycotoxin-ScFV-AP bifunctional fusion protein complex and a mycotoxin-ScFV-AP bifunctional fusion protein complex respectively by means of affinity reaction of streptavidin and biotin and antigen-antibody reaction. Magnetic particles directly precipitate in an external magnetic particle field, the complex is adsorbed at a bottom of a reagent tube through the magnetic particle field, free components are washed away, the substrate solution is added, the AP catalyzes hydrolysis of phosphate radical of the substrate, a decomposition reaction immediately occurs to release 475 nm of photons, and a relative light unit (RLU) of each sample hole is determined within 5 min. The RLU of the sample is negatively correlated with a concentration of the mycotoxin in the sample. The concentration of the mycotoxin in the sample is quantified according to a four-parameter mathematical model established from a concentrations of a mycotoxin standard and the corresponding RLU to test a content of the mycotoxin in the sample.

Further, a fully-automatic chemiluminescence immunoassay analyzer may be used for the above test, thereby fully-automatically testing the mycotoxins. The kits do not interfere with each other, and multiple samples can be tested simultaneously in real time, thereby highly satisfying the development requirements of quick field test of the mycotoxins. Furthermore, the kit of the disclosure used for testing the mycotoxins further has the following advantages: (1) A test speed is quick, stable and free of radioactive pollution; magnetic particles are suspended in a liquid under the condition that no magnetic particle field exists, such that the antigen-antibody reaction is similar to homogeneous reaction; and the magnetic particles can be conveniently separated and washed quickly under the action of the external magnetic particle field, and a test result may be determined within 24 min. (2) Sensitivity is high. (3) Specificity is high. (4) Precision is excellent. (5) A streptavidin and biotin cascade amplification system, the streptavidin magnetic particles, and the biotin-labeled mycotoxin antigen are directly linked to the mycotoxin antigen compared with the magnetic particles, such that reaction efficiency is greatly improved, and an operation is simple; and moreover, expiration date of the kit is increased, and it is confirmed through an accelerated stability test at 37° C. and a real stability test at 2° C.-8° C. that the product can be stored at 37° C. for 7 days or above, and can be stored for 1 year at 2° C.-8° C. (6) Cost is low, and compared with a similar product on the market, the kit has excellent performance, low cost and practical application value.

BRIEF DESCRIPTION OF DRAWINGS

The particular embodiments of the disclosure will be further described in detail below in combination with the accompanying drawings.

FIG. 1 is a schematic diagram of a magnetic chemiluminescence immunoassay based on a bifunctional fusion protein for mycotoxins.

DETAILED DESCRIPTION OF THE EMBODIMENTS

In order to illustrate the disclosure more clearly, the disclosure is further described below in combination with the examples and the accompanying drawings. In the accompanying drawings, the similar components are designated by the same reference numerals. Those skilled in the art should understand that the contents specifically described below are illustrative rather than restrictive, and should not limit the scope of protection of the disclosure.

The experimental materials used in the following examples, unless otherwise specified, are purchased by conventional biochemical reagent suppliers.

Example 1 Preparation of Aflatoxin B1 Nanobody—Alkaline Phosphatase Bifunctional Fusion Protein The AFB1-ScFV-AP bifunctional fusion protein was obtained by fusion expression of an AFB1 single-chain variable fragment (AFB1-ScFV) and an alkaline phosphatase (AP) by taking the alkaline phosphatase as a catalyst for bioluminescence.

The AFB1-ScFV-AP bifunctional fusion protein was prepared through the following method:

(1) An AFB1 single-chain variable fragment (ScFV) gene was designed and synthesized: according to an amino acid sequence SEQ ID NO:7 of the AFB1 nanobody, a structure of a gene was optimized to efficiently express the gene in *Escherichia coli* (*E. coli*) as follows: a preferred codon of the *E. coli* was used; a possible secondary structure was eliminated o, the GC/AT ratio was baanced. And a nucleotide fragment (nucleotide sequence shown as SEQ ID NO:8) of the AFB1 single-chain variable fragment (ScFV) gene was designed and synthesized.

(2) An AFB1-ScFV-AP expression vector was constructed: the AFB1 single-chain variable fragment (ScFV) gene synthesized in step (1) was cloned into a prokaryotic expression vector pET25b (+) to obtain pET25b (+)-ScFV; then an alkaline phosphatase expression vector pET25b (+)-AP (provided by Suzhou Hongxun Biotechnology Co., Ltd.) was digested with restriction enzymes XhoI and NotI to obtain an alkaline phosphatase gene fragment; and the alkaline phosphatase gene fragment was recovered by agrose gel and linked to the pET25b (+)-ScFV expression vector digested with the restriction enzymes XhoI and NotI through T4 DNA ligase in a molar ratio of 1:3. A linked product was transformed into *Escherichia coli* (*E. coli*) DH5u competent cells according to a heat shock method (42° C., 45 s), and transformed bacteria were inoculated into a lysogeny broth (LB) plate containing 100 μg/mL ampicillin (Amp), and cultured overnight at 37° C. Clones were primarily screened through colony polymerase chain reaction (PCR) and double enzyme digestion verification, screened positive clones were sequenced, and a bifunctional fusion expression vector AFB1-ScFV-AP was finally obtained.

(3) The AFB1-ScFV-AP bifunctional fusion protein was expressed: the bifunctional fusion expression vector was transformed into competent cells of an expression strain *E. coli* BL21 (Rosetta™, DE3) through heat shock, evenly spread on an LB plate containing 100 μg/mL Amp and 34 μg/mL chloramphenicol (CAP), and cultured upside down at 37° C. for 12 h. A single colony was selected and inoculated into a 5 mL LB/Amp/CAP liquid medium, and shaken and cultured at 37° C. and 220 rpm for 12 h; the culture was transferred to a 200 mL LB/Amp/CAP liquid medium according to 1% inoculation amount, and shaken and cultured at 37° C. and 220 rpm until an optical density 600 (OD600) was 0.4-0.6; isopropyl-β-d-thiogalactoside (IPTG) was added for induction culture, 1 mL of induced culture was transferred and centrifuged to collect bacterial cells, the bacterial cells were frozen at −20° C. for later use, and the remaining bacterial cells was collected by centrifugation at 5 000 g for 10 min; 4 mL of bacterial protein extraction reagent (B-PER) was added into each gram of the above bacterial cells, each ml of B-PER contained 2 μL lysozyme and 2 μL endonuclease DNase I, the bacteria were fully resuspended, and the bacteria stood at a room temperature for 10 min-15 min; and a supernatant containing a soluble protein was collected by centrifugation at 15000 g, 5 min, and expression of a target protein was analyzed according to sodium dodecyl sulfate-polyacrylamide gel electrophoresis (SDS-PAGE) and Western blot. Prokaryotic expression conditions were optimized by changing a final concentration (0 mmol/L-1 mmol/L, induction temperature 16° C.) of the IPTG and an induction temperature (16° C., 20° C., 30° C., 37° C., final concentration of IPTG 0.5 mmol/L) to explore an optimal expression condition of the fusion protein.

(4) The bifunctional fusion protein was purified and characterized: supernatant under the optimal expression condition was sterilized by a 0.45 μm sterile filter, loaded into a $Ni^{2+}$-NTA affinity column, washed with a ten times column bed volume of binding buffer (TBS buffer, pondus Hydrogenii (pH) 8.0), and eluted with binding buffers containing different concentrations of imidazole (20 mmol/L, 50 mmol/L, 100 mmol/L, 200 mmol/L) to collect elution components. Expression products and purification of the bifunctional fusion protein were characterized through 12% SDS-PAGE, and the gray scale of a gel picture was adjusted according to Image J software to analyze a protein band after elution by gray scale, so as to determine purity of the purified fusion protein.

According to the above method, the purified AFB1-ScFV-AP bifunctional fusion protein was finally obtained, and had an amino acid sequence shown as SED ID NO.1.

(5) Activity of the bifunctional fusion protein was analyzed:

Alkaline phosphatase activity of the bifunctional fusion protein was determined according to a disodium p-nitrophenyl phosphate method. 20 μL of the bifunctional fusion protein or the alkaline phosphatase diluted 50, 100, 200, 400, 800 and 1000 times were each added into an ELISA plate, then 100 μL p-nitrophenylphosphate (PNPP) reagent (2 mg/mL, dissolved into 0.1 M diethanolamine buffer containing 2 mM $MgCl_2$, pH 9.8) was added into holes, mixed evenly, and incubated at 37° C. for 10 min, 50 μL 4M NaOH solution was added to terminate reaction, absorbance at 405 nm was measured by a microplate reader, and concentrations (mM) of PNPP were calculated separately. Enzyme activity (U/mL)=PNPP concentration/reaction time*sample dilution multiple, and enzyme specific activity (U/mg)=enzyme activity (U/mL)/protein concentration (mg/mL). The alkaline phosphatase activity of the bifunctional fusion protein was evaluated by comparing the specific activity of the bifunctional fusion protein and the AP.

Antibody affinity of the bifunctional fusion protein was determined according to a biofilm interference technology. A sensor was balanced through a phosphate buffer saline (PBS) buffer for 60 s, and a biotin-labeled target mycotoxin was added for fixation and blocked through a PBST buffer (PBS buffer containing 0.02% Tween®-20, pH 7.4) for 180 s. Association and dissociation of the bifunctional fusion protein and the specific single-chain variable fragment (ScFV) with the target mycotoxin under different gradients were observed at a constant temperature of 30° C., association rate constant (Kon) values, dissociation rate constant (Koff) values and dissociation constant (KD) values (Kon value/Koff values) of the bifunctional fusion protein and the specific single-chain variable fragment (ScFV) with the target mycotoxin were calculated according to an Octet RED96e data processing program, and antibody affinity of the bifunctional fusion protein was characterized by comparing the KD values. Kon represented a formation rate of an antigen-antibody complex, and the larger the Kon value was, the quicker antigen-antibody association was; Koff reflected stability of the formed complex, and the larger the Koff value was, the quicker complex dissociation was; and KD may reflect the size of an association capability of interaction between an antigen and an antibody, and when the KD value reaches $10^{-8}$ mol/L, it was indicated that the antigen and the antibody had extremely high affinity.

Example 2 Preparation of Deoxynivalenol Single-Chain Variable Fragment (ScFV)-Alkaline Phosphatase Bifunctional Fusion Protein A DON-ScFV-AP bifunctional fusion protein was prepared through the method of Example 1, and had an amino acid sequence shown as SED ID NO:2.

Example 3 Preparation of Zearalenone Single-Chain Variable Fragment (ScFV)-Alkaline Phosphatase Bifunctional Fusion Protein A ZEN-ScFV-AP bifunctional fusion protein was prepared through the method of Example 1, and had an amino acid sequence shown as SED ID NO:3.

Example 4 Preparation of T-2 Toxin Single-Chain Variable Fragment (ScFV)-Alkaline Phosphatase Bifunctional Fusion Protein A T-2-ScFV-AP bifunctional fusion protein was prepared through the method of Example 1, and had an amino acid sequence shown as SED ID NO:4.

Example 5 Preparation of Fumonisin B1 Single-Chain Variable Fragment (ScFV)-Alkaline Phosphatase Bifunctional Fusion Protein An FB1-ScFV-AP bifunctional fusion protein was prepared through the method of Example 1, and had an amino acid sequence shown as SED ID NO:5.

Example 6 Preparation of Ochratoxin a Single-Chain Variable Fragment (ScFV)-Alkaline Phosphatase Bifunctional Fusion Protein An OTA-ScFV-AP bifunctional fusion protein was prepared through the method of Example 1, and had an amino acid sequence shown as SED ID NO:6.

Example 7 Preparation of Magnetic Chemiluminescence Immunoassay Kit for AFB1

1. Streptavidin magnetic particles were prepared:
(1) magnetic particles were dispersed: 10 mg of magnetic particles were dispersed through 10 mL of 0.1 M 2-morpholineethanesulfonic acid solution (MES buffer) to make a final concentration of the magnetic particles be 1 mg/mL;
(2) the magnetic particles were cleaned: the magnetic particles were cleaned with a 2-morpholinoethanesulphonic acid (MES) buffer having 3 times volume of the magnetic particle solution, and then re-dispersed with the MES buffer to make a final concentration of the magnetic particles be 1 mg/mL;
(3) the magnetic particles were activated and linked: 3 mg of streptavidin and 3.5 µL of 10 mg/mL carbodiimide hydrochloride solution were sequentially added into a magnetic particle dispersion liquid obtained in step (2), and stirred at a room temperature for reaction for 2 h;
(4) the magnetic particles were blocked: the magnetic particles in step (3) were separated from a reaction system, washed with the MES buffer twice, and re-dispersed with the MES buffer, where the magnetic particles had a final concentration of 2 mg/ml-30 mg/mL; and then 2% glycine blocking solution was added, and stirred at the room temperature for reaction for 2 h;
(5) the magnetic particles were cleaned: the magnetic particles in step (4) were separated from the reaction system, and magnetic particle beads were cleaned with a phosphate buffer having a pH value of 7.4 twice to obtain the streptavidin magnetic particles; and
(6) during use, the streptavidin magnetic particles were prepared into a streptavidin magnetic particle working solution: the streptavidin magnetic particles in step (5) were dispersed into a phosphate buffer containing 0.5 g/mL casein, 1 g/mL polyethylene glycol 200 (PEG200), 0.2% Tween®-20 and 0.5% bovine serum albumin, where a pH value was 7-8, and the magnetic particles had a final concentration of 1 mg/mL.

2. A biotin-labeled AFB1 antigen was prepared:
(1) AFB1 and carboxymethyl hydroxylamine hemihydrochloride were placed into pyridine, and stirred in dark at the room temperature for reaction for 24 h to obtain a first reaction solution;
(2) the first reaction solution was frozen and dried to obtain a solid dry substance;
(3) the solid dry substance was dissolved with pure water, a pH value was adjusted to 3.0 with hydrochloric acid, and precipitate was extracted with ethyl acetate, and dried in vacuum to obtain AFB1 oxime;
(4) the AFB1 oxime was dissolved into a pyridine solution of KOH, and 1-(3-dimethylaminopropyl)-3-ethylcarbodiimide hydrochloride was added for reaction at 70° C. for 12 h to obtain a second reaction solution;
(5) N-hydroxysuccinimide was added into the second reaction solution, and stirred at the room temperature for reaction for 2 h to obtain a third reaction solution;
(6) cationic bovine serum albumin was dissolved with distilled water, added into the third reaction solution, and stirred in dark at the room temperature for reaction for 24 h to obtain a fourth reaction solution;
(7) the fourth reaction solution was dialyzed in 0.01 mol/L phosphate buffer for 3 days, and dialysate was frozen and dried to obtain an AFB1-bovine serum albumin complex;
(8) the AFB1-bovine serum albumin complex was mixed with a PBS buffer, and activated biotin was added for labeling for 2 h, and dialyzed to obtain the biotin-labeled AFB1 antigen; and
(9) during use, the biotin-labeled AFB1 antigen was diluted with 0.01M phosphate buffer and 0.5% bovine serum albumin solution in a ratio of 1:15000 to obtain a biotin-labeled AFB1 antigen working solution.

3. An AFB1-ScFV-AP bifunctional fusion protein working solution was prepared:
the AFB1-ScFV-AP bifunctional fusion protein prepared in Example 1 was diluted with 0.01 M tris-salt buffer and 0.5% bovine serum albumin solution in a ratio of 1:20000 to obtain the AFB1-ScFV-AP bifunctional fusion protein working solution.

4. A sample diluent was prepared:
the sample diluent consisted of 0.01 M phosphate buffer, 0.1% Tween®-20 and 0.5% bovine serum albumin.

5. A washing solution was prepared:
the washing solution consisted of 0.01 M tris-HCl buffer and 0.10% Tween®-20.

6. An AFB1 standard solution was prepared:
an AFB1 standard was diluted with a methanol-water (50:50) solution to working concentrations of 0.25 ng/mL, 0.5 ng/mL, 1 ng/mL, 2.5 ng/mL, 5 ng/mL, 10 ng/mL and 20 ng/mL separately, i.e. concentrations of standard points.
7. A substrate solution was prepared:
(4-chlorophenylmercapto)(10-methyl-9,10-dihydroacridomethylene) phosphate disodium salt was diluted with 0.01 M PBS to obtain a 1 mmol/L substrate solution.
8. Assembly was carried out: the above reagents were assembled into a kit and stored at 2° C.-8° C.

A schematic diagram of magnetic chemiluminescence immunoassay based on the bifunctional fusion protein for AFB1 was shown in FIG. 1.

Example 8 Methodological Investigation of Magnetic Chemiluminescence Immunoassay Kit for AFB1 in Test of AFB1

Methodological investigation test for test of AFB1 was carried out on the magnetic chemiluminescence immunoassay kit for AFB1 prepared in Example 7.

(1) A stability test was carried out: the magnetic chemiluminescence immunoassay kit for AFB1 was treated through an advanced stabilizer (0.01 M phosphate buffer, 0.1% bovine serum albumin solution, 0.1% proclin 300 and 1% trehalose), and stored at 37° C. after treatment for an accelerated stability test to obtain a stability result shown in Table 1. According to experience, storage at 37° C. for 1 day was equivalent to storage at 4° C. for 2 months. That is, the kit was stored at 4° C. for 12 months without affecting use.

(2) Sensitivity was analyzed:
by measuring 20 independent corn negative samples, a limit of detection (LOD) of the method was calculated by a mean of 20 determination results of the negative samples plus 3 times standard deviation, and a result was 0.2 µg/kg. A limit of quantitation (LOQ) was calculated by the mean of 20 determination results of the negative samples plus 10 times standard deviation, and a result was 1.0 µg/kg.

(3) A linear relation was investigated:
① a standard curve was drawn: four-parameter fitting was carried out according to concentration-relative light unit series values of the AFB1 standard solution to obtain a concentration-relative light unit standard curve; and
② a sample concentration was calculated: the relative light unit was inversely proportional to a concentration of the AFB1 antigen within a certain range, and the content of the AFB1 of the sample to be tested was calculated according to a fitted concentration-relative light unit standard curve of the AFB1.

(4) Specificity of the magnetic chemiluminescence immunoassay kit for AFB1 was investigated:
the magnetic chemiluminescence immunoassay kit for AFB1 was configured to test structural analogues (AFB1, AFB2, AFG1 and AFG2) and other common mycotoxins (DON; FB1; FB2; fumonisin B3 (FB3); ZEN; T-2; OTA; 3-acetyldeoxynivalenol (3-ADON); 15-acetyldeoxynivalenol (15-ADON); deoxynivalenol-3-glucoside (DON-3G); and nivalenol (NIV)), and results were shown in Table 1. Only AFB2 and AFG1 had obvious cross-reaction with the cross-reaction rates of 26.3% and 23.8% respectively, and other toxins had no cross-reaction (a cross-reaction rate was less than 1%), which indicated that the magnetic chemiluminescence immunoassay kit for AFB1 had excellent specificity.

TABLE 1

Investigation of specificity of magnetic chemiluminescence immunoassay kit for AFB1

| Serial number | Mycotoxin | IC50 | Cross-reaction rate (%) |
|---|---|---|---|
| 1 | $AFB_1$ | 0.5 ppb | — |
| 2 | $AFB_2$ | 1.9 ppb | 26.3 |
| 3 | $AFG_1$ | 2.1 ppb | 23.8 |
| 4 | $AFG_2$ | 8.1 ppb | 6.2 |
| 5 | DON | >10 ppm | <1% |
| 6 | $FB_1$ | >28.6 ppm | <1% |
| 7 | $FB_2$ | >28.6 ppm | <1% |
| 8 | $FB_3$ | >28.6 ppm | <1% |
| 9 | ZEN | >20 ppm | <1% |
| 10 | T-2 | >100 ppm | <1% |
| 11 | OTA | >1.9 ppm | <1% |
| 12 | 3-ADON | >100.1 ppm | <1% |
| 13 | 15-ADON | >100.4 ppm | <1% |
| 14 | DON-3G | >50 ppm | <1% |
| 15 | NIV | >100.4 ppm | <1% |

Example 9 Use of Magnetic Chemiluminescence Immunoassay Kit for AFB1

(1) A sample to be tested was pretreated: 5.0 g of crushed sample to be tested was weighed into a 50 mL centrifuge tube, a 25.0 mL methanol/water (70:30) solution was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 µL of an extract of the sample to be tested was added into the test tube, and then centrifuged at 7000 rpm for 5 min to obtain an extract of the sample to be tested.

(2) The magnetic chemiluminescence immunoassay kit for AFB1 (prepared in Example 7) was used as follows:
① physical inspection was carried out: a liquid component should be clarified without precipitation or flocculae; and other components should be free of packaging damage;
② the kit was balanced at a room temperature (2° C.-8° C.) for 30 min; and
③ a sample was determined: 40 L-200 µL of the extract of the sample to be tested was added into a sample hole, and was placed into a fully-automatic chemiluminescence immunoassay analyzer. The fully-automatic chemiluminescence immunoassay analyzer was clicked for running, and 50 µL of the extract of the sample to be tested or AFB1 standard solution, 50 µL of streptavidin magnetic particle working solution, 50 µL of AFB1 single-chain variable fragment (ScFV)-alkaline phosphatase bifunctional fusion protein and 400 µL of diluent were sequentially added into the instrument according to a preset running program, mixed evenly, incubated at 37° C. for 5 min, and sequentially washed 3 times. A relative light unit was measured, and results were analyzed according to an internally-set four-parameter fitting curveDetermination of 8 samples may be completed within 20 min, and a detection report may be provided.

(3) Accuracy and repeatability of the magnetic chemiluminescence immunoassay kit for AFB1 were determined:

5 g of negative brown rice, rice, corn, peanut butter, wheat and peanut oil samples were weighed separately, different amounts of AFB1 standards were added, and 7 parallels were constituted, and determined through a magnetic chemiluminescence immunoassay kit for AFB1-labeled sample extract. Recovery rates, means and relative standard deviations (RSDs) of the 7 parallels were shown in Tables 2, 3, 4, 5, 6 and 7. The recovery rate was between 79.1% and 120%, and the RSD was less than 10%.

TABLE 2

Recovery rate and repeatability of AFB1 in brown rice determined by magnetic chemiluminescence immunoassay kit for AFB1

| Serial number | Indicated value | | | | | | | |
|---|---|---|---|---|---|---|---|---|
| | 5.15 µg/Kg | | 10.3 µg/Kg | | 20.1 µg/Kg | | 30 µg/Kg | |
| | Signal value | Recovery rate | Signal value | Recovery rate | Signal value | Recovery rate | Signal value | Recovery rate |
| 7 parallels | 569002 | 101.7 | 394952 | 87.0 | 173922 | 109.2 | 138127 | 91.5 |
| | 633812 | 83.4 | 388373 | 88.9 | 182473 | 104.2 | 129496 | 97.2 |
| | 611780 | 89.3 | 390910 | 88.1 | 183611 | 103.6 | 118455 | 105.6 |
| | 582410 | 97.7 | 385162 | 89.8 | 165338 | 114.8 | 131402 | 95.9 |
| | 554910 | 106.2 | 372985 | 93.5 | 169166 | 112.2 | 134564 | 93.8 |
| | 585885 | 96.7 | 364413 | 96.2 | 178032 | 106.8 | 127625 | 98.6 |
| | 590135.2 | 95.8 | 383785 | 90.2 | 177944 | 106.8 | 127241 | 98.8 |
| Average | 589704.9 | 95.8 | 382940 | 90.5 | 175783.7 | 108.2 | 129558.6 | 97.3 |
| RSD | 4.45 | 7.87 | 2.79 | 3.59 | 3.83 | 3.80 | 4.82 | 4.61 |

TABLE 3

Recovery rate and repeatability of rice determined by magnetic chemiluminescence immunoassay kit for AFB1

| Serial number | Adding standard matter amount | | | | | |
|---|---|---|---|---|---|---|
| | 4.5 µg/Kg | | 9.5 µg/Kg | | 18.0 µg/Kg | |
| | Signal value | Recovery rate | Signal value | Recovery rate | Signal value | Recovery rate |
| 7 parallels | 474052 | 114.6 | 353713 | 83.5 | 151702 | 101.4 |
| | 503165 | 105.0 | 355778 | 83.0 | 145944 | 105.0 |
| | 540414 | 93.7 | 354265 | 83.3 | 149911 | 102.5 |
| | 466730 | 117.2 | 332555 | 89.4 | 149587 | 102.7 |
| | 533923 | 95.6 | 342152 | 86.6 | 130351 | 114.7 |
| | 528072 | 97.3 | 342288 | 86.6 | 128450 | 118.7 |
| | 518085 | 100.3 | 323142 | 92.2 | 150255 | 102.3 |
| Average | 509205.8 | 103.4 | 343413.3 | 86.4 | 141800 | 106.7 |
| RSD | 5.72 | 9.00 | 3.58 | 4.00 | 6.93 | 6.53 |

TABLE 4

Recovery rate and repeatability of corn determined by magnetic chemiluminescence immunoassay kit for AFB1

| Serial number | Adding standard matter amount | | | | | |
|---|---|---|---|---|---|---|
| | 10.7 µg/Kg | | 24 µg/Kg | | 45 µg/Kg | |
| | Signal value | Recovery rate | Signal value | Recovery rate | Signal value | Recovery rate |
| 7 parallels | 242095 | 82.1 | 88745 | 104.8 | 52154 | 90.4 |
| | 212075 | 94.2 | 92385 | 100.8 | 50501 | 93.6 |
| | 249536 | 80.1 | 90033 | 103.4 | 49035 | 96.6 |
| | 212834 | 93.9 | 84790 | 109.5 | 49708 | 95.2 |
| | 232691 | 85.6 | 93454 | 99.7 | 47068 | 101.0 |
| | 242359 | 82.0 | 94203 | 99.0 | 48721 | 97.2 |
| | 255799 | 77.4 | 89682 | 103.7 | 53529 | 88.0 |
| Average | 235341.3 | 85.0 | 90470.3 | 103.0 | 50102.3 | 94.6 |
| RSD | 7.30 | 7.79 | 3.57 | 3.51 | 4.35 | 4.60 |

TABLE 5

Recovery rate and repeatability of peanut butter determined by magnetic chemiluminescence immunoassay kit for AFB1

| Serial number | Adding standard matter amount | | | | | | | |
|---|---|---|---|---|---|---|---|---|
| | 13.0 µg/Kg | | 24.0 µg/Kg | | 44.0 µg/Kg | | 50 µg/Kg | |
| | Signal value | Recovery rate | Signal value | Recovery rate | Signal value | Recovery rate | Signal value | Recovery rate |
| 7 parallels | 569002 | 101.7 | 394952 | 87.0 | 173922 | 109.2 | 138127 | 91.5 |
| | 633812 | 83.4 | 388373 | 88.9 | 182473 | 104.2 | 129496 | 97.2 |
| | 611780 | 89.3 | 390910 | 88.1 | 183611 | 103.6 | 118455 | 105.6 |
| | 582410 | 97.7 | 385162 | 89.8 | 165338 | 114.8 | 131402 | 95.9 |
| | 554910 | 106.2 | 372985 | 93.5 | 169166 | 112.2 | 134564 | 93.8 |
| | 585885 | 96.7 | 364413 | 96.2 | 178032 | 106.8 | 127625 | 98.6 |
| | 590135.2 | 95.8 | 383785 | 90.2 | 177944 | 106.8 | 127241 | 98.8 |
| Average | 589704.9 | 95.8 | 382940 | 90.5 | 175783.7 | 108.2 | 129558.6 | 97.4 |
| RSD | 4.45 | 7.87 | 2.79 | 3.59 | 3.83 | 3.80 | 4.82 | 4.61 |

TABLE 6

Recovery rate and repeatability of wheat determined by magnetic chemiluminescence immunoassay kit for AFB1

| Serial number | Adding standard matter amount | | | | | | | |
|---|---|---|---|---|---|---|---|---|
| | 2.5 µg/Kg | | 5 µg/Kg | | 10 µg/Kg | | 20 µg/Kg | |
| | Signal value | Recovery rate | Signal value | Recovery rate | Signal value | Recovery rate | Signal value | Recovery rate |
| 7 parallels | 478354 | 94.3 | 287195 | 93.7 | 161260 | 93.5 | 105350 | 79.1 |
| | 474691 | 95.4 | 292499 | 91.6 | 161785 | 93.2 | 104682 | 79.8 |
| | 484646 | 92.4 | 275836 | 98.5 | 164485 | 91.4 | 95578 | 90.0 |
| | 461235 | 99.6 | 275562 | 98.6 | 163129 | 92.3 | 101661 | 82.9 |
| | 480621 | 93.6 | 279540 | 96.9 | 153211 | 99.5 | 102349 | 82.2 |
| | 458847 | 100.3 | 267653 | 102.2 | 164952 | 91.1 | 102763 | 81.8 |
| | 456390 | 101.1 | 275526 | 98.6 | 156222 | 97.2 | 93455 | 92.8 |
| Average | 470683.4 | 96.7 | 279116 | 97.1 | 160721 | 94.0 | 100834 | 84.1 |
| RSD | 2.46 | 3.70 | 2.97 | 3.61 | 2.73 | 3.34 | 4.51 | 6.22 |

TABLE 7

Recovery rate and repeatability of peanut oil determined by magnetic chemiluminescence immunoassay kit for AFB1

| Serial number | Adding standard matter amount | | | | | |
|---|---|---|---|---|---|---|
| | 13.0 µg/Kg | | 20.8 µg/Kg | | 34.6 µg/Kg | |
| | Signal value | Recovery rate | Signal value | Recovery rate | Signal value | Recovery rate |
| 7 parallels | 165055 | 94.0 | 80941 | 92.2 | 50505 | 106.3 |
| | 169370 | 91.5 | 82981 | 89.6 | 50902 | 105.0 |
| | 167594 | 92.5 | 78758 | 95.3 | 49332 | 110.7 |
| | 162956 | 95.2 | 74660 | 101.6 | 48652 | 113.4 |
| | 166690 | 93.0 | 74939 | 101.2 | 49422 | 108.6 |
| | 169976 | 91.2 | 78049 | 96.3 | 49828 | 105.6 |
| | 169020 | 91.7 | 74720 | 101.5 | 49524 | 107.1 |
| Average | 167237.3 | 92.7 | 77864 | 96.8 | 19737.9 | 108.1 |
| RSD | 1.52 | 1.57 | 4.23 | 5.01 | 1.52 | 2.81 |

Example 10 Methodological Investigation of
Magnetic Chemiluminescence Immunoassay Kit for
DON in Test of DON Methodological investigation test for test of DON was carried out on the magnetic chemiluminescence immunoassay kit for DON prepared in Example 7.

(1) A stability test was carried out: the magnetic chemiluminescence immunoassay kit for DON was treated through an advanced stabilizer (0.01 M phosphate buffer, 0.1% bovine serum albumin solution, 0.1% proclin 300 and 1% trehalose), and stored at 37° C. after treatment for an accelerated stability test to obtain a stability result shown in Table 1. According to experience, storage at 37° C. for 1 day was equivalent to storage at 4° C. for 2 months. That is, the kit was stored at 4° C. for 12 months without affecting use.

(2) Sensitivity was analyzed:
- by measuring 20 independent corn negative samples, an LOD of the method was calculated by a mean of 20 determination results of the negative samples plus 3 times standard deviation, and a result was 77.0 µg/kg. An LOQ was calculated by the mean of 20 determination results of the negative samples plus 10 times standard deviation, and a result was 222.8 µg/kg.

(3) A linear relation was investigated:
① a standard curve was drawn: four-parameter fitting was carried out according to concentration-relative light unit series values of the DON standard solution to obtain a concentration-relative light unit standard curve; and
② a sample concentration was calculated: within a certain range, the relative light unit was inversely proportional to a concentration of the DON antigen, and the content of the DON of the sample to be tested was calculated according to a fitted concentration-relative light unit standard curve of the DON.

(4) Specificity of the magnetic chemiluminescence immunoassay kit for DON was investigated:
the magnetic chemiluminescence immunoassay kit for DON was configured to test structural analogues (3-ADON; 15-ADON; and NIV) and other common mycotoxins (AFB1, DON, ZEN, T-2 and OTA), and results were shown in Table 8. Only 3-ADON had obvious cross-reaction, and other toxins had no cross-reaction, which indicated that the magnetic chemiluminescence immunoassay kit for DON had excellent specificity.

TABLE 8

Specificity of magnetic chemiluminescence immunoassay kit for DON

| Serial number | Mycotoxin | IC50 | Cross-reaction rate (%) |
|---|---|---|---|
| 1 | DON | 2.4 ppb | — |
| 2 | AFB1 | >2 ppm | <1% |
| 3 | T-2 | >100 ppm | <1% |
| 4 | OTA | >1.9 ppm | <1% |
| 5 | ZEN | >20 ppm | <1% |
| 6 | 3-ADON | 2.3 ppb | 104.3% |
| 7 | 15-ADON | 64 ppb | 3.7% |
| 8 | NIV | 610 ppb | <1% |

Example 11 Use of Magnetic Chemiluminescence
Immunoassay Kit for DON (1) A sample to be tested was pretreated: 5.0 g of crushed sample to be tested was weighed into a 50 mL centrifuge tube, 25.0 mL water was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 µL of an extract of the sample to be tested was added into the test tube, and then centrifuged at 7000 rpm for 5 min to obtain an extract of the sample to be tested.

(2) The magnetic chemiluminescence immunoassay kit for DON was used as follows:
① physical inspection was carried out: a liquid component should be clarified without precipitation or floccule; and other components should be free of packaging damage;
② the kit to be tested was balanced at a room temperature (2° C.-8° C.) for 30 min; and
③ a sample was determined: 40 µL-200 µL of the extract of the sample to be tested was added into a sample hole, the sample hole was placed into a fully-automatic chemiluminescence immunoassay analyzer, the fully-automatic chemiluminescence immunoassay analyzer was clicked for running, 50 µL of the extract of the sample to be tested or DON standard solution, 50 µL of streptavidin magnetic particle working solution, 50 µL of DON-ScFV-AP bifunctional fusion protein and 400 µL of diluent were sequentially added into the instrument according to a preset running program, mixed evenly, and incubated at 37° C. for 5 min, and sequentially washed 3 times, a relative light unit was measured, results were analyzed according to an internally-set four-parameter fitting curve, determination of 8 samples may be completed within 20 min, and a detection report may be provided.

(3) Accuracy and repeatability of the magnetic chemiluminescence immunoassay kit for DON were determined:
5 g of negative corn, wheat and flour samples were weighed separately, different amounts of DON standards were added, and 7 parallels were constituted, and determined through a magnetic chemiluminescence immunoassay kit for DON-labeled sample extract. Recovery rates, means and RSDs of the 7 parallels were shown in Tables 9, 10 and 11. The recovery rate was between 80% and 120%, and the RSD was less than 9%.

TABLE 9

Recovery rate and repeatability of DON in corn determined by magnetic chemiluminescence immunoassay kit for DON

| | Adding standard matter amount | | | | | | | |
|---|---|---|---|---|---|---|---|---|
| | 462 µg/Kg | | 1077 µg/Kg | | 2076 µg/Kg | | 3849.9 µg/Kg | |
| Serial number | Signal value | Recovery rate | Signal value | Recovery rate | Signal value | Recovery rate | Signal value | Recovery rate |
| 7 parallels | 84268 | 113.0 | 53224 | 101.8 | 31989 | 97.8 | 25493 | 87.0 |
| | 81996 | 118.8 | 52560 | 103.7 | 32054 | 96.6 | 25887 | 85.5 |
| | 85378 | 110.3 | 52624 | 103.5 | 34363 | 86.8 | 24717 | 91.8 |
| | 86861 | 106.8 | 45043 | 129.9 | 35462 | 82.8 | 24933 | 90.4 |
| | 81216 | 119.1 | 51934 | 105.5 | 31688 | 98.2 | 25474 | 87.1 |
| | 81739 | 112.1 | 49802 | 112.2 | 35843 | 81.5 | 24515 | 93.2 |
| | 81541 | 114.6 | 52544 | 103.7 | 31180 | 100.2 | 24176 | 95.5 |
| Average | 83285.6 | 113.5 | 51104.43 | 108.6 | 33225.6 | 92.0 | 25170.71 | 89.2 |
| RSD | 2.66 | 3.91 | 5.66 | 9.20 | 5.8 | 8.7 | 3.56 | 5.89 |

TABLE 10

Recovery rate and repeatability of DON in wheat determined by magnetic chemiluminescence immunoassay kit for DON

| | Adding standard matter amount | | | | | | | |
|---|---|---|---|---|---|---|---|---|
| | 462 µg/Kg | | 1077 µg/Kg | | 2076 µg/Kg | | 3849.9 µg/Kg | |
| Serial number | Signal value | Recovery rate | Signal value | Recovery rate | Signal value | Recovery rate | Signal value | Recovery rate |
| 7 parallels | 465727 | 87.2 | 278629 | 100.1 | 178835 | 98.0 | 113078 | 92.4 |
| | 445893 | 96.6 | 274721 | 102.4 | 167670 | 106.6 | 109075 | 96.2 |
| | 446779 | 96.2 | 278010 | 100.4 | 170160 | 104.6 | 104783 | 100.6 |
| | 429863 | 104.9 | 261318 | 110.6 | 174383 | 101.36 | 107950 | 97.3 |
| | 425158 | 107.4 | 260273 | 111.3 | 170294 | 104.5 | 107644 | 97.6 |
| | 430248 | 104.7 | 262468 | 109.9 | 166443 | 107.6 | 106103 | 99.2 |
| | 435931 | 101.7 | 259488 | 111.8 | 169332 | 105.26 | 112577 | 92.8 |
| Average | 439942.7 | 99.8 | 267843.9 | 106.6 | 171016.7 | 104.0 | 108744.3 | 96.6 |
| RSD | 3.18 | 7.01 | 3.29 | 5.06 | 2.49 | 3.15 | 2.86 | 3.19 |

TABLE 11

Recovery rate and repeatability of DON in flour determined by magnetic chemiluminescence immunoassay kit for DON

| | Adding standard matter amount | | | | | | | |
|---|---|---|---|---|---|---|---|---|
| | 293.8 µg/Kg | | 415.1 µg/Kg | | 1218.8 µg/Kg | | 1732.3 µg/Kg | |
| Serial number | Signal value | Recovery rate | Signal value | Recovery rate | Signal value | Recovery rate | Signal value | Recovery rate |
| 7 parallels | 589341 | 100.5 | 534991 | 89.8 | 296580 | 84.3 | 222302 | 92.6 |
| | 573702 | 107.7 | 537047 | 89.0 | 307199 | 79.9 | 196035 | 114.2 |
| | 573794 | 106.4 | 530234 | 91.6 | 288450 | 87.9 | 215486 | 97.4 |
| | 583709 | 103.1 | 499507 | 103.8 | 272370 | 95.9 | 205223 | 105.6 |
| | 574694 | 107.2 | 506134 | 101.0 | 276471 | 93.7 | 207131 | 104.0 |
| | 563299 | 112.6 | 496854 | 104.9 | 275319 | 94.3 | 214958 | 97.8 |
| | 575301 | 107.0 | 537829 | 88.8 | 283927 | 90.0 | 205827 | 105.1 |
| Average | 576262.9 | 106.4 | 520370.9 | 95.6 | 285759.4 | 89.4 | 209566 | 102.4 |
| RSD | 1.44 | 3.58 | 3.58 | 7.66 | 4.43 | 6.53 | 4.12 | 6.94 |

Example 12 Use of Magnetic Chemiluminescence Immunoassay Kit for ZEN

Reference was made to the magnetic chemiluminescence immunoassay kit for ZEN prepared in Example 7.

(1) A sample to be tested was pretreated: 5.0 g of crushed sample to be tested was weighed into a 50 mL centrifuge tube, 25.0 mL 80% acetonitrile aqueous solution was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 μL of an extract of the sample to be tested was added into the test tube, and then centrifuged at 7000 rpm for 5 min to obtain an extract of the sample to be tested.

(2) The magnetic chemiluminescence immunoassay kit for ZEN was used as follows:

① physical inspection was carried out: a liquid component should be clarified without precipitation or floccule; and other components should be free of packaging damage;

② the kit to be tested was balanced at a room temperature (2° C.-8° C.) for 30 min; and ③ a sample was determined: 40 μL-200 μL of the extract of the sample to be tested was added into a sample hole, the sample hole was placed into a fully-automatic chemiluminescence immunoassay analyzer, the fully-automatic chemiluminescence immunoassay analyzer was clicked for running, 50 μL of the extract of the sample to be tested or ZEN standard solution, 50 μL of streptavidin magnetic particle working solution, 50 μL of ZEN-ScFV-AP bifunctional fusion protein and 400 μL of diluent were sequentially added into the instrument according to a preset running program, mixed evenly, and incubated at 37° C. for 5 min, and sequentially washed 3 times, a relative light unit was measured, results were analyzed according to an internally-set four-parameter fitting curve, determination of 8 samples may be completed within 20 min, and a detection report may be provided.

(3) Sensitivity of the magnetic chemiluminescence immunoassay kit for ZEN was analyzed:

by measuring 20 independent corn negative samples, an LOD of the method was calculated by a mean of 20 determination results of the negative samples plus 3 times standard deviation, and a result was 3.9939 μg/kg. An LOQ was calculated by the mean of 20 determination results of the negative samples plus 10 times standard deviation, and a result was 9.4483 μg/kg.

(4) Accuracy and repeatability of the magnetic chemiluminescence immunoassay kit for ZEN were determined:

5 g of negative corn, wheat, brown rice and flour samples were weighed separately, different amounts of ZEN standards were added, and 7 parallels were constituted, and determined through a magnetic chemiluminescence immunoassay kit for ZEN-labeled sample extract. Recovery rates, means and RSDs of the 7 parallels were shown in Tables 12, 13, 14 and 15. The recovery rate was between 80% and 20, and the RSD was less than 10%.

TABLE 12

Accuracy and repeatability of ZEN in corn determined by magnetic chemiluminescence immunoassay kit for ZEN

| | Indicated value | | | | | |
| --- | --- | --- | --- | --- | --- | --- |
| | 40 μg/kg | | 65 μg/kg | | 120 μg/kg | |
| Serial number | Signal value | Recovery rate | Signal value | Recovery rate | Signal value | Recovery rate |
| 7 parallels | 510744 | 100.0 | 341985 | 85.9 | 178761 | 102.8 |
| | 526307 | 96.0 | 290650 | 103.6 | 161792 | 115.0 |
| | 453876 | 112.1 | 296218 | 101.3 | 161575 | 115.0 |
| | 484728 | 106.4 | 273630 | 110.5 | 160058 | 116.3 |
| | 493256 | 104.6 | 307608 | 96.9 | 160797 | 115.0 |
| | 501753 | 102.1 | 295336 | 101.8 | 161040 | 117.4 |
| | 490395 | 105.1 | 295280 | 101.8 | 165325 | 108.2 |
| Average | 491300.5 | 105.3 | 300101.0 | 100.2 | 164192.6 | 112.8 |
| RSD | 6.5 | 8.6 | 7.0 | 7.5 | 4.0 | 4.7 |

TABLE 13

Accuracy and repeatability of ZEN in wheat determined by magnetic chemiluminescence immunoassay kit for ZEN

| | Indicated value | | | | | |
| --- | --- | --- | --- | --- | --- | --- |
| | 40 μg/kg | | 83 μg/kg | | 112.1 μg/kg | |
| Serial number | Signal value | Recovery rate | Signal value | Recovery rate | Signal value | Recovery rate |
| 7 parallels | 453852 | 102.3 | 244610 | 94.1 | 197133 | 89.9 |
| | 467348 | 99.2 | 242325 | 94.6 | 192349 | 91.7 |
| | 423284 | 110.4 | 203450 | 109.3 | 183333 | 94.8 |
| | 475243 | 97.0 | 210606 | 106.2 | 169963 | 100.2 |

TABLE 13-continued

Accuracy and repeatability of ZEN in wheat determined
by magnetic chemiluminescence immunoassay kit for ZEN

| | Indicated value | | | | | |
|---|---|---|---|---|---|---|
| | 40 µg/kg | | 83 µg/kg | | 112.1 µg/kg | |
| Serial number | Signal value | Recovery rate | Signal value | Recovery rate | Signal value | Recovery rate |
| | 512840 | 88.72 | 248766 | 92.6 | 181786 | 95.4 |
| | 481451 | 95.7 | 212905 | 102.6 | 212395 | 85.6 |
| | 475668 | 97.0 | 223650 | 101.8 | 220118 | 82.4 |
| Average | 469955.1 | 98.6 | 226616 | 100.2 | 193868.1 | 91.4 |
| RSD | 5.8 | 6.7 | 8.16 | 8.2 | 9.1 | 6.7 |

TABLE 14

Accuracy and repeatability of ZEN in brown rice determined
by magnetic chemiluminescence immunoassay kit for ZEN

| | Indicated value | | | | | |
|---|---|---|---|---|---|---|
| | 40 µg/kg | | 65 µg/kg | | 120 µg/kg | |
| Serial number | Signal value | Recovery rate | Signal value | Recovery rate | Signal value | Recovery rate |
| 7 parallels | 423564 | 98.9 | 377962 | 88.8 | 178501 | 98.6 |
| | 438770 | 96.9 | 333806 | 102.4 | 169753 | 104.1 |
| | 422683 | 100.5 | 321223 | 106.9 | 181334 | 96.9 |
| | 448702 | 93.2 | 363184 | 93.0 | 181229 | 97.0 |
| | 453160 | 92.0 | 318690 | 107.8 | 179656 | 97.9 |
| | 472120 | 87.2 | 375178 | 89.6 | 181549 | 96.8 |
| | 457053 | 91.0 | 358564 | 94.4 | 183461 | 95.7 |
| Average | 445150.29 | 94.2 | 349801.0 | 97.6 | 179354.7 | 98.1 |
| RSD | 4.1 | 5.02 | 7.1 | 8.2 | 2.5 | 2.9 |

TABLE 15

Accuracy and repeatability of ZEN in flour determined
by magnetic chemiluminescence immunoassay kit for ZEN

| | Indicated value | | | | | |
|---|---|---|---|---|---|---|
| | 36.1 µg/kg | | 69.1 µg/kg | | 116 µg/kg | |
| Serial number | Signal value | Recovery rate | Signal value | Recovery rate | Signal value | Recovery rate |
| 7 parallels | 406982 | 94.0 | 248164 | 97.2 | 129851 | 107.1 |
| | 389049 | 99.6 | 210095 | 114.8 | 157683 | 91.3 |
| | 379865 | 102.4 | 223893 | 107.6 | 150830 | 93.2 |
| | 454869 | 81.1 | 243108 | 99.1 | 148829 | 94.6 |
| | 371740 | 105.0 | 222968 | 108.1 | 119087 | 116.1 |
| | 376188 | 103.5 | 227776 | 105.9 | 145524 | 96.7 |
| | 369435 | 106.5 | 247513 | 97.2 | 155837 | 90.5 |
| Average | 392589.7 | 98.9 | 231931.0 | 104.3 | 143948.7 | 98.5 |
| RSD | 7.7 | 9.0 | 6.3 | 6.4 | 9.9 | 9.7 |

Example 13 Use of Magnetic Chemiluminescence Immunoassay Kit for T-2

Reference was made to the magnetic chemiluminescence immunoassay kit for T-2 prepared in Example 7.

(1) A sample to be tested was pretreated: 5.0 g of crushed negative corn sample was weighed into a 50 mL centrifuge tube, different amounts of T-2 standards were added separately, final spike levels were 47.8 µg/Kg and 108 µg/Kg separately, 7 parallels were constituted, 25.0 mL 80% acetonitrile aqueous solution was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 µL of an extract of the sample to be tested was added into the test tube, and then centrifuged at 7000 rpm for 5 min to obtain an extract of the sample to be tested.

(2) The magnetic chemiluminescence immunoassay kit for T-2 was used as follows:

① physical inspection was carried out: a liquid component should be clarified without precipitation or floccule; and other components should be free of packaging damage;

② the kit to be tested was balanced at a room temperature (2° C.-8° C.) for 30 min; and ③ a sample was determined: 40 L-200 μL of the extract of the sample to be tested was added into a sample hole, the sample hole was placed into a fully-automatic chemiluminescence immunoassay analyzer, the fully-automatic chemiluminescence immunoassay analyzer was clicked for running, 50 μL of the extract of the sample to be tested or T-2 standard solution, 50 μL of streptavidin magnetic particle working solution, 50 μL of T-2-ScFV-AP bifunctional fusion protein and 400 μL of diluent were sequentially added into the instrument according to a preset running program, mixed evenly, and incubated at 37° C. for 5 min, and sequentially washed 3 times, a relative light unit was measured, results were analyzed according to an internally-set four-parameter fitting curve, determination of 8 samples may be completed within 20 min, and a detection report may be provided.

(3) Accuracy and repeatability of the magnetic chemiluminescence immunoassay kit for T-2 were determined:

the extract of the sample to be tested obtained in step (1) was determined through the magnetic chemiluminescence immunoassay kit for T-2. Recovery rates, means and RSDs of the 7 parallels were shown in Table 16. The recovery rate was between 89.0% and 107.5%, and the RSD was less than 3%.

TABLE 16

Accuracy and repeatability of magnetic chemiluminescence immunoassay kit for T-2

| | Adding standard matter amount | | | |
|---|---|---|---|---|
| | 47.8 μg/Kg | | 108 μg/Kg | |
| Serial number | Signal value | Recovery rate | Signal value | Recovery rate |
| 7 parallels | 255783 | 107.5 | 115482 | 89.0 |
| | 256350 | 107.3 | 114527 | 89.6 |
| | 263113 | 104.9 | 110796 | 92.0 |
| | 270066 | 102.5 | 110558 | 92.1 |
| | 271727 | 102.0 | 109032 | 93.2 |
| | 269879 | 102.6 | 106813 | 94.7 |
| | 265105 | 104.2 | 105315 | 95.8 |
| Average | 264574.7 | 104.5 | 110360.4 | 92.4 |
| RSD | 2.5 | 2.2 | 3.4 | 2.7 |

Example 14 Use of Magnetic Chemiluminescence Immunoassay Kit for FB1

Reference was made to the magnetic chemiluminescence immunoassay kit for FB1 prepared in Example 7.

(1) A sample to be tested was pretreated: 5.0 g of crushed negative corn sample was weighed into a 50 mL centrifuge tube, different amounts of FB1 standards were added separately, final spike levels were 47.8 μg/Kg and 108 μg/Kg separately, and 7 parallels were constituted, 25.0 mL 80% acetonitrile aqueous solution was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 μL of an extract of the sample to be tested was added into the test tube, and then centrifuged at 7000 rpm for 5 min to obtain an extract of the sample to be tested.

(2) The magnetic chemiluminescence immunoassay kit for FB1 was used as follows:

① physical inspection was carried out: a liquid component should be clarified without precipitation or floccule; and other components should be free of packaging damage;

② the kit to be tested was balanced at a room temperature (2° C.-8° C.) for 30 min; and ③ a sample was determined: 40 μL-200 μL of the extract of the sample to be tested was added into a sample hole, the sample hole was placed into a fully-automatic chemiluminescence immunoassay analyzer, the fully-automatic chemiluminescence immunoassay analyzer was clicked for running, 50 μL of the extract of the sample to be tested or FB1 standard solution, 50 μL of streptavidin magnetic particle working solution, 50 μL of FB1-ScFV-AP bifunctional fusion protein and 400 μL of diluent were sequentially added into the instrument according to a preset running program, mixed evenly, and incubated at 37° C. for 5 min, and sequentially washed 3 times, a relative light unit was measured, results were analyzed according to an internally-set four-parameter fitting curve, determination of 8 samples may be completed within 20 min, and a detection report may be provided.

(3) Accuracy and repeatability of the magnetic chemiluminescence immunoassay kit for FB1 were determined:

the extract of the sample to be tested obtained in step (1) was determined through the magnetic chemiluminescence immunoassay kit for FB1. Recovery rates, means and RSDs of the 7 parallels were shown in Table 17. The recovery rate was between 89.2% and 111.3%, and the RSD was less than 6%.

TABLE 17

Accuracy and repeatability of magnetic chemiluminescence immunoassay kit for FB1

| | Adding standard matter amount | | | | | |
|---|---|---|---|---|---|---|
| | 1291 μg/Kg | | 2473 μg/Kg | | 3884 μg/Kg | |
| Serial number | Signal value | Recovery rate | Signal value | Recovery rate | Signal value | Recovery rate |
| 7 parallels | 998851 | 96.5 | 600233 | 100.2 | 414602 | 110.4 |
| | 939704 | 104.7 | 652892 | 89.2 | 441313 | 100.0 |
| | 1030187 | 92.6 | 646962 | 90.3 | 430623 | 103.9 |
| | 981362 | 98.8 | 594188 | 101.6 | 416362 | 109.6 |
| | 923178 | 107.2 | 624057 | 94.9 | 420974 | 107.7 |
| | 972359 | 100.0 | 634352 | 92.8 | 412568 | 111.3 |
| | 997931 | 96.6 | 565930 | 108.8 | 431924 | 103.4 |

TABLE 17-continued

Accuracy and repeatability of magnetic chemiluminescence immunoassay kit for FB1

| | Adding standard matter amount | | | | | |
|---|---|---|---|---|---|---|
| | 1291 μg/Kg | | 2473 μg/Kg | | 3884 μg/Kg | |
| Serial number | Signal value | Recovery rate | Signal value | Recovery rate | Signal value | Recovery rate |
| Average | 977653.1 | 99.5 | 616944.9 | 96.8 | 424052.3 | 106.6 |
| RSD | 3.8 | 5.1 | 5.1 | 7.3 | 2.5 | 4.0 |

Example 15 Use of Magnetic Chemiluminescence Immunoassay Kit for OTA

Reference was made to the magnetic chemiluminescence immunoassay kit for OTA prepared in Example 7.

(1) A sample to be tested was pretreated: 5.0 g of crushed sample was weighed into a 50 mL centrifuge tube, 25.0 mL 80% acetonitrile aqueous solution was added, the centrifuge tube was placed on a multi-tube vortex mixer and vortexed at 2500 rpm for 5 min (or homogenized at 11000 rpm for 3 min through a high-speed homogenizer, or shaken at 200 rpm for 40 min on a shaker), and 20 μL of an extract of the sample to be tested was added into the test tube, and then centrifuged at 7000 rpm for 5 min to obtain an extract of the sample to be tested.

(2) The magnetic chemiluminescence immunoassay kit for OTA was used as follows:
  ① physical inspection was carried out: a liquid component should be clarified without precipitation or floccule; and other components should be free of packaging damage;
  ② the kit to be tested was balanced at a room temperature (2° C.-8° C.) for 30 min; and
  ③ a sample was determined: 40 μL-200 μL of the extract of the sample to be tested was added into a sample hole, the sample hole was placed into a fully-automatic chemiluminescence immunoassay analyzer, the fully-automatic chemiluminescence immunoassay analyzer was clicked for running, 50 μL of the extract of the sample to be tested or OTA standard solution, 50 μL of streptavidin magnetic particle working solution, 50 μL of OTA-ScFV-AP bifunctional fusion protein and 400 μL of diluent were sequentially added into the instrument according to a preset running program, mixed evenly, and incubated at 37° C. for 5 min, and sequentially washed 3 times, a relative light unit was measured, results were analyzed according to an internally-set four-parameter fitting curve, determination of 8 samples may be completed within 20 min, and a detection report may be provided.

(3) Sensitivity of the magnetic chemiluminescence immunoassay kit for OTA was analyzed:
  by measuring 20 independent wheat negative samples, an LOD of the method was calculated by a mean of 20 determination results of the negative samples plus 3 times standard deviation, and a result was 2.0610 μg/kg. An LOQ was calculated by the mean of 20 determination results of the negative samples plus 10 times standard deviation, and a result was 4.5105 μg/kg.

(4) Accuracy and repeatability of the magnetic chemiluminescence immunoassay kit for OTA were determined:
  5 g of negative corn, wheat and brown rice samples were weighed separately, different amounts of OTA standards were added, and 7 parallels were constituted, and determined through a magnetic chemiluminescence immunoassay kit for OTA-labeled sample extract. Recovery rates, means and RSDs of the 7 parallels were shown in Tables 18, 19 and 20. The recovery rate was between 80% and 120%, and the RSD was less than 8%.

TABLE 18

Accuracy and repeatability of OTA in corn determined by magnetic chemiluminescence immunoassay kit for OTA

| | Adding standard matter amount | | | | | |
|---|---|---|---|---|---|---|
| | 2.5 μg/kg | | 5 μg/kg | | 10 μg/kg | |
| Serial number | Signal value | Recovery rate (%) | Signal value (%) | Recovery rate (%) | Signal value (%) | Recovery rate (%) |
| 7 parallels | 560202 | 87.4 | 257026 | 101.2 | 77474 | 91.1 |
| | 551812 | 89.6 | 258742 | 100.7 | 76867 | 91.3 |
| | 505945 | 102.8 | 251411 | 103.0 | 71790 | 93.0 |
| | 516824 | 99.5 | 253978 | 102.2 | 73081 | 92.5 |
| | 510085 | 101.5 | 243849 | 105.4 | 71419 | 93.1 |
| | 519847 | 98.6 | 233175 | 108.9 | 71391 | 93.1 |
| | 533170 | 94.8 | 244708 | 105.1 | 76680 | 91.4 |
| Average | 528269.3 | 96.3 | 248984.1 | 103.8 | 74100.3 | 92.2 |
| RSD | 4.0 | 6.2 | 3.6 | 2.8 | 3.8 | 1.0 |

TABLE 19

Accuracy and repeatability of OTA in wheat determined by magnetic chemiluminescence immunoassay kit for OTA

| | Adding standard matter amount | | | | | |
|---|---|---|---|---|---|---|
| | 2.5 µg/kg | | 4.5 µg/kg | | 10 µg/kg | |
| Serial number | Signal value | Recovery rate (%) | Signal value (%) | Recovery rate (%) | Signal value (%) | Recovery rate (%) |
| 7 parallels | 593533 | 94.4 | 287701 | 107.4 | 91050 | 89.3 |
| | 585922 | 96.8 | 273263 | 111.2 | 92530 | 89.0 |
| | 601552 | 92.7 | 288797 | 107.1 | 87627 | 90.2 |
| | 659779 | 80.7 | 273621 | 111.1 | 86140 | 90.6 |
| | 619662 | 88.8 | 271031 | 111.8 | 89546 | 89.7 |
| | 577659 | 98.0 | 256957 | 115.7 | 77388 | 92.9 |
| | 641436 | 84.3 | 271934 | 111.6 | 84777 | 90.9 |
| Average | 611363.3 | 90.8 | 274757.7 | 110.8 | 87008.3 | 90.4 |
| RSD | 5.0 | 7.1 | 4.0 | 2.6 | 5.8 | 1.4 |

TABLE 20

Recovery rate and repeatability of OTA in brown rice determined by magnetic chemiluminescence immunoassay kit for OTA

| | Adding standard matter amount | | | | | |
|---|---|---|---|---|---|---|
| | 2.5 µg/kg | | 5 µg/kg | | 10 µg/kg | |
| Serial number | Signal value | Recovery rate | Signal value | Recovery rate | Signal value | Recovery rate |
| 7 parallels | 387474 | 87.3 | 155443 | 102.2 | 45842 | 91.3 |
| | 385128 | 88.0 | 163563 | 98.7 | 42316 | 93.5 |
| | 397676 | 84.3 | 154122 | 102.8 | 43737 | 92.6 |
| | 379549 | 89.7 | 154879 | 102.5 | 39489 | 95.4 |
| | 384442 | 88.2 | 142438 | 108.3 | 41438 | 94.1 |
| | 361000 | 95.6 | 159948 | 100.2 | 43925 | 92.5 |
| | 346553 | 100.4 | 144718 | 107.2 | 41150 | 94.3 |
| Average | 377403.1 | 90.5 | 153587.3 | 103.1 | 42556.7 | 93.4 |
| RSD | 4.6 | 6.1 | 5.0 | 3.4 | 5.0 | 1.5 |

Obviously, the above examples of the disclosure are only examples for clearly illustrating the disclosure, and are not intended to limit the embodiments of the disclosure. Those of ordinary skill in the pertinent field can further make other different forms of changes or variations on the basis of the above description, and all the embodiments cannot be exhausted herein. Any obvious changes or variations derived from the technical solutions of the disclosure still fall within the scope of protection of the disclosure.

REFERENCE TO AN ELECTRONIC SEQUENCE LISTING

The contents of the electronic sequence listing (JAN-56074.xml; Size: 12061 bytes; and Date of Creation: Jun. 19, 2024) is herein incorporated by reference in its entirety.

What is claimed is:

1. A magnetic chemiluminescence immunoassay kit for mycotoxins, comprising streptavidin magnetic particles, a biotin-labeled mycotoxin antigen, a mycotoxin standard solution, a mycotoxin single-chain variable fragment (ScFV)-alkaline phosphatase bifunctional fusion protein, a sample diluent, a washing solution and a substrate solution; wherein the mycotoxin single-chain variable fragment (ScFV)-alkaline phosphatase bifunctional fusion protein is obtained by fusion expression of a mycotoxin single-chain variable fragment (ScFV) and an alkaline phosphatase by using the alkaline phosphatase as a catalyst for bioluminescence;

the mycotoxin single-chain variable fragment (ScFV) is selected from heavy chain antibodies of camelids or sharks; and the mycotoxin single-chain variable fragment (ScFV)-alkaline phosphatase bifunctional fusion protein has an amino acid sequence of an aflatoxin B1 single-chain variable fragment (ScFV)-alkaline phosphatase bifunctional fusion protein shown as SEQ ID NO:1.

2. The kit according to claim 1, wherein the mycotoxin single-chain variable fragment (ScFV)-alkaline phosphatase bifunctional fusion protein is prepared through the following method:

(1) designing and synthesizing a mycotoxin single-chain variable fragment (ScFV) gene: optimizing, according to an amino acid sequence of the mycotoxin single-chain variable fragment (ScFV), a structure of a gene to efficiently express the gene in Escherichia coli (E. coli) as follows: using a preferred codon of the E. coli, eliminating a possible secondary structure, achieving GC/AT balance, and designing and synthesizing a nucleotide fragment of the mycotoxin single-chain variable fragment (ScFV) gene;

(2) constructing a mycotoxin single-chain variable fragment (ScFV)-alkaline phosphatase bifunctional fusion expression vector: cloning the mycotoxin single-chain variable fragment (ScFV) gene synthesized in step (1) and an alkaline phosphatase gene into a prokaryotic expression vector to construct the mycotoxin single-chain variable fragment (ScFV)-alkaline phosphatase bifunctional fusion expression vector;

(3) expressing the mycotoxin single-chain variable fragment (ScFV)-alkaline phosphatase bifunctional fusion protein: transforming the bifunctional fusion expression vector into competent cells of an expression strain E. coli to induce expression, collecting bacterial cells, adding a bacterial protein extraction reagent, and centrifugally collecting supernatant containing a soluble protein; and (4) purifying the bifunctional fusion protein: purifying the fusion protein according to a $Ni^{2+}$-NTA affinity column.

3. The kit according to claim 1, wherein peripheries of magnetic particles are coated with polystyrene or dextran by taking a ferroferric oxide or ferric oxide superparamagnetic material as a core, the magnetic particles are activated according to a physical or chemical method to generate —$NH_2$, tosyl, —COOH or —CH(O) groups on surfaces of the magnetic particles, and the magnetic particles have a particle size ranging from 1 μm to 2 μm.

4. The kit according to claim 1, wherein the streptavidin magnetic particles are obtained by coupling streptavidin with magnetic particles.

5. The kit according to claim 1, wherein the biotin-labeled mycotoxin antigen is obtained by coupling mycotoxins with bovine serum albumin, and then coupling an obtained bovine serum albumin-mycotoxin complex with biotin.

6. The kit according to claim 1, wherein the mycotoxin standard solution is prepared by dissolving a mycotoxin standard into a methanol-water mixed solution.

7. The kit according to claim 1, wherein a volume ratio of methanol to water in the methanol-water mixed solution is 20:80-80:20.

8. The kit according to claim 1, wherein the substrate solution is sodium ((4-chlorophenyl)thio)(10-methyl-9,10-dihydroacridin-9(10H)-ylidene)methyl phosphate solution having a concentration ranging from 0.5 mmol/L to 2 mmol/L.

9. The kit according to claim 1, wherein the sample diluent consists of 0.01 M phosphate buffer, 0.1% Polyoxyethylene (20) sorbitan monolaurate and 0.5% bovine serum albumin.

10. The kit according to claim 1, wherein the washing solution consists of 0.01 M tris-HCl buffer and 0.1% Polyoxyethylene (20) sorbitan monolaurate.

11. The kit according to claim 1, wherein the kit further comprises a reaction tube.

12. The kit according to claim 1, wherein the reaction tube is made of transparent polystyrene, polyethylene, polypropylene or glass.

13. A method for testing mycotoxins using the kit of claim 1, comprising:
 obtaining a sample to be tested;
 adding in sequence:
  the sample or a mycotoxin standard solution,
  streptavidin magnetic particle working solution,
  mycotoxin single-chain variable fragment (ScFV)-alkaline phosphatase bifunctional fusion protein, and
  a diluent;
 mixing and incubating;
 washing;
 measuring chemiluminescence; and
 determining mycotoxin content based on the measured chemiluminescence.

14. The method according to claim 13, wherein a use of the kit in test of mycotoxins in edible oil, food, grain, feed or Chinese herbal medicine.

15. The method according to claim 14, wherein the edible oil comprises one of peanut oil, corn oil, soybean oil, rapeseed oil, sunflower oil, rapeseed oil, sesame oil and olive oil.

16. The method according to claim 13, wherein the mycotoxins are tested through a fully-automatic mycotoxin analyzer.

17. The method according to claim 13, wherein the mycotoxins comprise one or more of aflatoxin, zearalenone, deoxynivalenol, fumonisin, ochratoxin A and T-2 toxin.

* * * * *